United States Patent [19]

Tsunekawa et al.

[11] Patent Number: 5,036,347
[45] Date of Patent: Jul. 30, 1991

[54] VISUAL LINE DETECTING DEVICE AND CAMERA HAVING THE SAME

[75] Inventors: Tokuichi Tsunekawa; Akihiko Nagano, both of Kanagawa; Kazuki Konishi, Tokyo, all of Japan

[73] Assignee: Canon Kabushiki Kaisha, Tokyo, Japan

[21] Appl. No.: 393,594

[22] Filed: Aug. 14, 1989

[30] Foreign Application Priority Data

Aug. 31, 1988 [JP] Japan .................. 63-216674

[51] Int. Cl.⁵ ............................ G03B 13/36
[52] U.S. Cl. .................... 354/400; 354/62; 354/195.1; 354/219
[58] Field of Search ............ 354/400, 402, 403, 404, 354/195.1, 219, 62

[56] References Cited

U.S. PATENT DOCUMENTS

| | | | |
|---|---|---|---|
| 4,574,314 | 3/1986 | Weinblatt | 354/400 |
| 4,828,381 | 5/1989 | Shindo | 354/62 |
| 4,836,670 | 6/1989 | Hutchinson | 354/62 |

FOREIGN PATENT DOCUMENTS

0040112 2/1988 Japan .................. 354/400

Primary Examiner—Russell E. Adams, Jr.
Attorney, Agent, or Firm—Robin, Blecker, Daley & Driscoll

[57] ABSTRACT

A visual line detecting device is arranged to detect the Purkinje image position of an illuminated eye of an observer through light reflected by the eye and to detect the direction of the visual line of the observer from the Purkinje image position and the position of the pupil center of the eye. The device estimates the pupil diameter of the eye from the luminance of external light and determines the position of the center of the pupil by determining the position of a boundary between the pupil and the iris of the eye on the basis of the pupil diameter estimated.

25 Claims, 12 Drawing Sheets

VISUAL LINE DETECTING DEVICE AND CAMERA HAVING THE SAME

BACKGROUND OF THE INVENTION

1. Field of the Invention

This invention relates to a visual line detecting device and to a camera having the visual line detecting device.

2. Description of the Related Art

A visual line detecting device which optically detects the line of sight (visual axis) of an observer has been disclosed in Japanese Laid-Open Patent Application No. SHO 61-172552.

Figure 9:
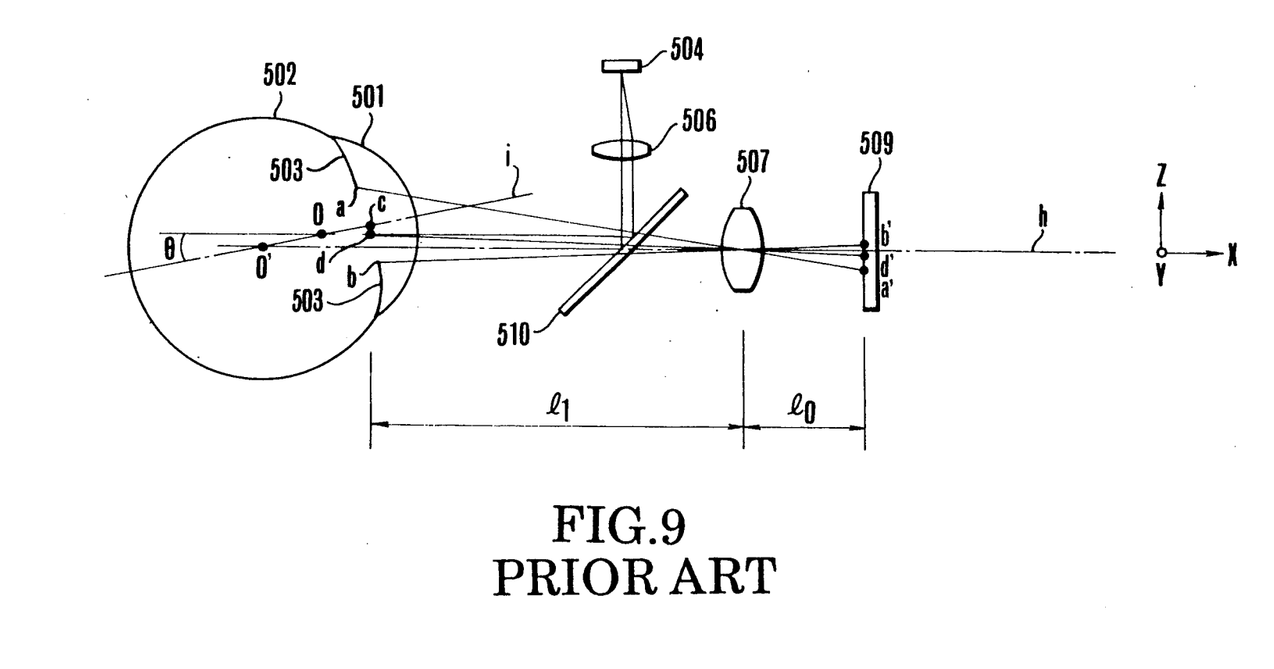
FIG. 9 shows in outline the arrangement of the conventional visual line detecting device for detecting the line by using a reflection image of a cornea and the center of a pupil.

This device is arranged to detect the visual line of the observer on the basis of the position of the center of a pupil and a first Purkinje image which is a reflection image obtained from the front surface of a cornea and which is generated by irradiating the eyeball of the observer with parallel rays of light. FIG. 9 of the accompanying drawings shows this.

Referring to FIG. 9, the illustration includes a cornea 501; a sclera 502; an iris 503; a light source 504; a light projecting lens 506; a light receiving lens 507; an image sensor 509; a half-mirror 510; a rotation center O' of the eyeball; the center of curvature O of the cornea 501; end parts "a" and "b" of the iris 503; the center "c" of the iris 503; a point "d" where a first Purkinje image is generated; the optical axis "h" of the light receiving lens 507, which coincides with the X-axis shown in FIG. 9; and the optical axis "i" of the eyeball.

The light source 504 is an infrared ray emitting diode which is arranged on the focal plane of the light projecting lens 506 to emit infrared rays insensible to the observer. The infrared rays emitted from the light source 504 become parallel rays through the light projecting lens 506 and are then reflected by the half-mirror 510 to illuminate the cornea 501. A part of the infrared rays reflected by the surface of the cornea 501 passes through the half-mirror 510 to be formed into an image at a point d' on the image sensor 509 by the light receiving lens 507. The end parts "a" and "b" of the iris 503 are imaged through the half-mirror 510 and the light receiving lens 507 at points a' and b' on the image sensor 509. Assuming that the Z-coordinates of the end parts "a" and "b" of the iris 503 are Za and Zb, the coordinate Zc of the center point "c" of the iris 503 can be expressed as follows when the rotation angle $\theta$ of the optical axis "i" of the eyeball relative to the optical axis "h" of the light receiving lens 507 is small:

$$Zc \approx \frac{Za + Zb}{2}$$

Further, assuming that the Z-coordinate of the first Purkinje image generating point "d" is Zd and a distance from the curvature center $\overline{O}$ of the cornea 501 to the center "c" of the iris 503 is $\overline{oc}$, the rotation angle $\theta$ of the optical axis "i" of the eyeball approximately satisfies the following formula:

$$\overline{oc} \cdot \sin \theta \approx Zc - Zd \quad (1)$$

Therefore, the rotation angle $\theta$ of the optical axis "i" of the eyeball can be found by detecting specific points (the first Purkinje image Zd' and the end parts Za' and Zb' of the iris 503) projected and obtained on the image sensor 509. Formula (1) above is rewritten as follows:

$$\beta \cdot \overline{oc} \cdot \sin \theta \approx Za' + Zb'/2 - Zd'$$

wherein: $\beta$ represents a magnifying rate determined by a distance 11 between the first Purkinje image generating point "d" and the light receiving lens 507 and a distance 10 between the light receiving lens 507 and the image sensor 509. This rate $\beta$ is normally a constant value.

The direction of the line of sight is detectable according to the principle described above.

However, the visual line detecting device described has presented the following problem: The reflection factor of the cornea is about 2.5%. The light quantity of the reflection image of the cornea is large enough to have its location detected without fail. Whereas, the reflection factor of the iris is very small and a contrast at the boundary between the iris and the pupil is insufficient. Therefore, in actuality, it has been difficult to accurately determine the position of the pupil center.

Further, assuming that the visual line detecting device is employed in a camera and arranged, for example, to detect a point looked at by the photographer within the viewfinder of the camera and that a focusing action is carried out according to the result of detection, a distance between the eye and the visual line detecting system in the direction of the optical axis of the viewfinder optical system varies with the camera holding state of the photographer. As a result, therefore, a reflection image coming from the eyeball might blur to further deteriorate the characteristic of a detection signal thus obtained. A camera actually using such a visual line detecting device for automatic focusing has been known from U.S. Pat. No. 4,574,314 (Weinblatt).

SUMMARY OF THE INVENTION

It is one aspect of this invention to provide a visual line detecting device which is arranged to detect the pupil center position from a deteriorated signal as accurately as possible.

DETAILED DESCRIPTION OF THE PREFERRED EMBODIMENT

The details of this invention will become apparent from the following description of an embodiment given with reference to the accompanying drawings:

The principle of this invention will be first described with reference to FIGS. 2 and 3.

Figure 1:
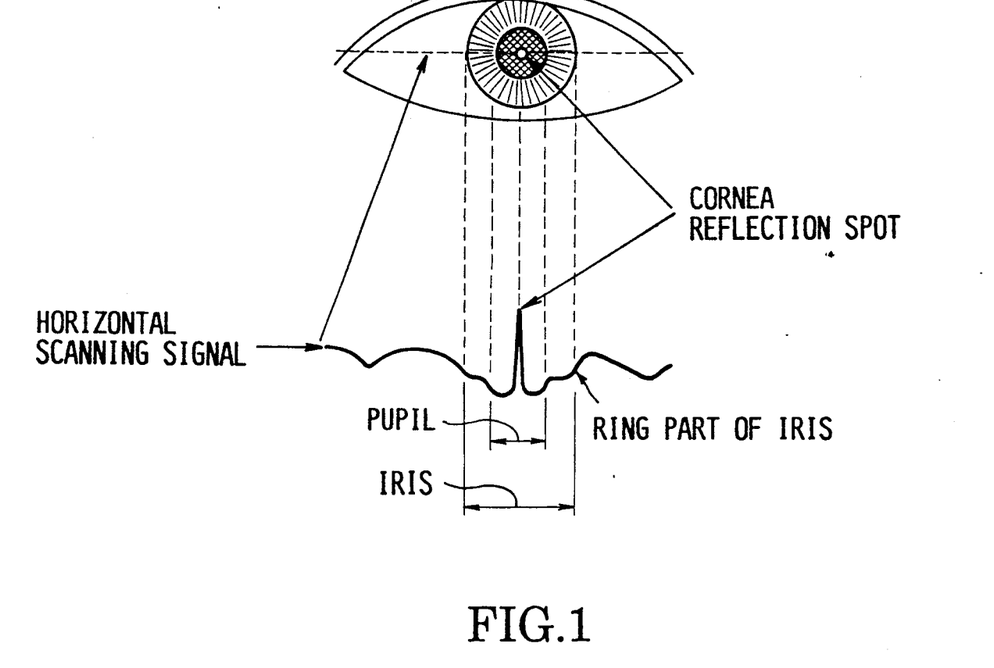
FIG. 1 shows a horizontal scanning signal corresponding to the position of an eyeball.

FIG. 1 shows a horizontal scanning signal which corresponds to the position of an eyeball obtained when the central part of the eyeball is horizontally scanned with light applied to the eyeball to have a reflection image formed on a linear or area type photo-electric conversion element such as a CCD. As apparent from the drawing, while the reflection image of a cornea is accurately detectable because of a strong contrast, other tissues have low boundary contrast. It is, therefore, not easy to accurately detect a boundary between an iris and a pupil and a boundary between the black and white parts of the eye, that is, the ring-like part of the iris. However, it is known that the pupil of the human eye changes its diameter according to the brightness of light in a given relation to the latter.

Figure 2:
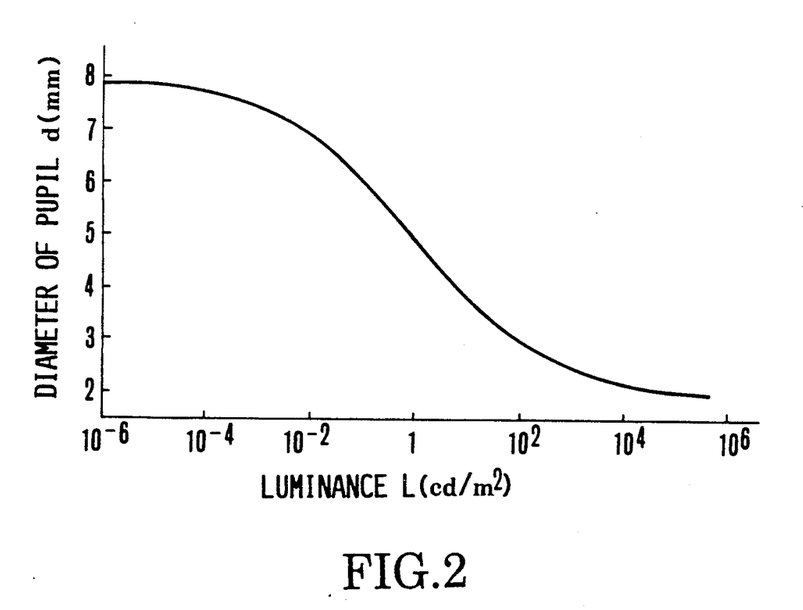
FIG. 2 shows a relation between luminance and the diameter of a pupil.

FIG. 2 shows in a graph the relation between a luminance representing the brightness of external light and the diameter of the pupil. Generally, the pupil diameter changes in relation to the luminance as shown in FIG. 2 although the changing degree somewhat varies among people. The human eye has a luminance measuring part which forms an image on the retina. The eye is arranged to have the diameter of the pupil controlled by information from this luminance measuring part.

The invented device detects the visual line position of the eye through information on the diameter of the pupil obtained from the output of a luminance meter (exposure meter) which is employed in a camera or the like and is arranged to measure changes taking place in the brightness of external light.

Figure 3:
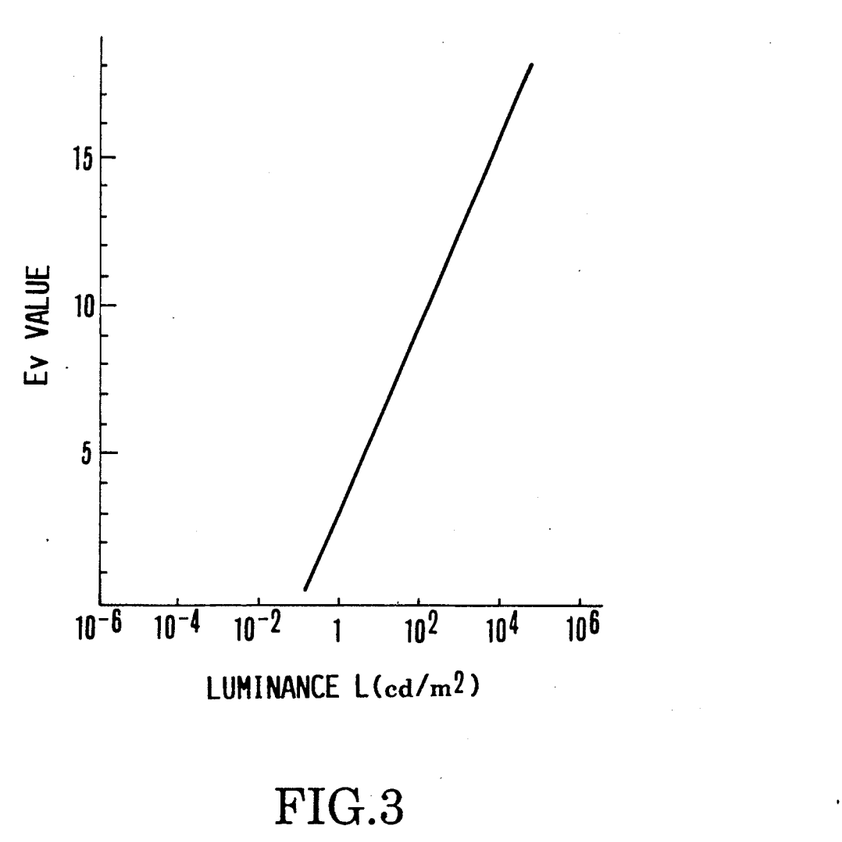
FIG. 3 shows the characteristic of the luminance meter (exposure meter) of a camera.

FIG. 3 shows the characteristic of the luminance meter (exposure meter) of the camera. An Ev value is a result of the light measuring action of a light measuring circuit of the camera as will be further described later. The relation of the Ev value to the luminance L of the external light is as shown in FIG. 3.

Figure 4:
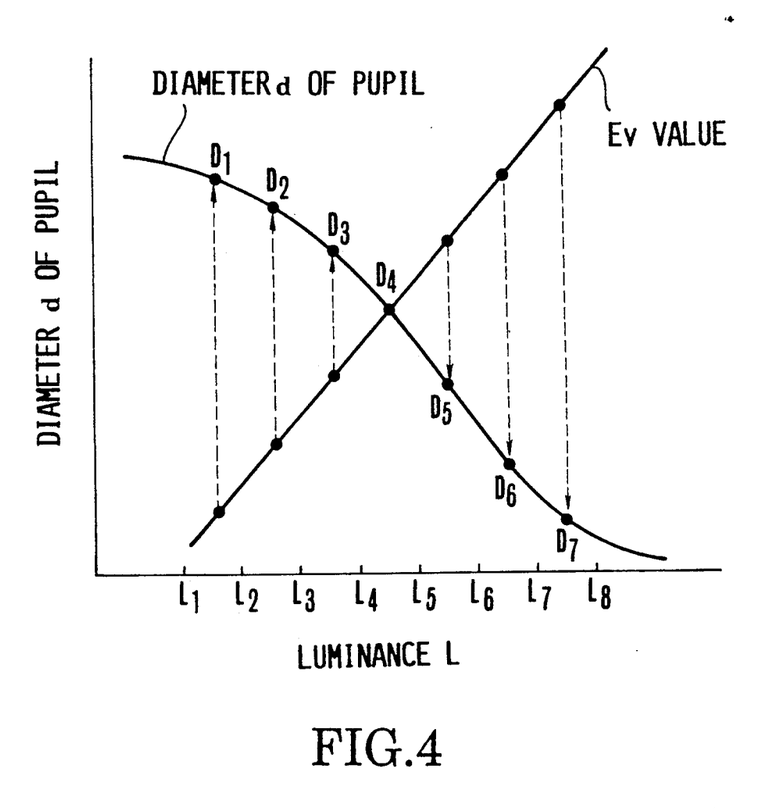
FIG. 4 is a graph showing a map for obtaining the pupil diameter from the luminance meter of the camera.

FIG. 4 shows by way of example a map for obtaining the diameter of the pupil from the luminance meter of the camera. Information on the pupil diameter corresponding to the luminance of external to the eye can be obtained by mapping the pupil diameter, for example, to be D1 for a luminance value between L1 and L2, to be D2 for a luminance value between L2 and L3 and so on. The luminance value points L1, L2,—may be spaced at any suitable distance. With respect to the relation of the outside (ambient) luminance L ($cd/m^2$) to the pupil diameter d (mm) as shown in FIG. 2, the relation is known, for example, to become as follows in accordance with the formula of Crawford:

$$d = 5 - 3 \tanh(0.4 \log L)$$

Meanwhile, it is known that the Ev value of the camera can be expressed by the following formula:

$$2^{Ev} = \frac{S}{K} \times L$$

wherein S represents a film sensitivity value and K a calibrating constant of the exposure meter.

A pupil diameter value corresponding to each Ev value measured by the exposure meter of the camera can be obtained from the formulas shown above.

The Ev value obtained by the exposure meter corresponds to the brightness of the viewfinder of the camera. Therefore, the Ev value gives information to be used in determining the pupil diameter which is obtained when the photographer looks into the viewfinder.

Figure 5:
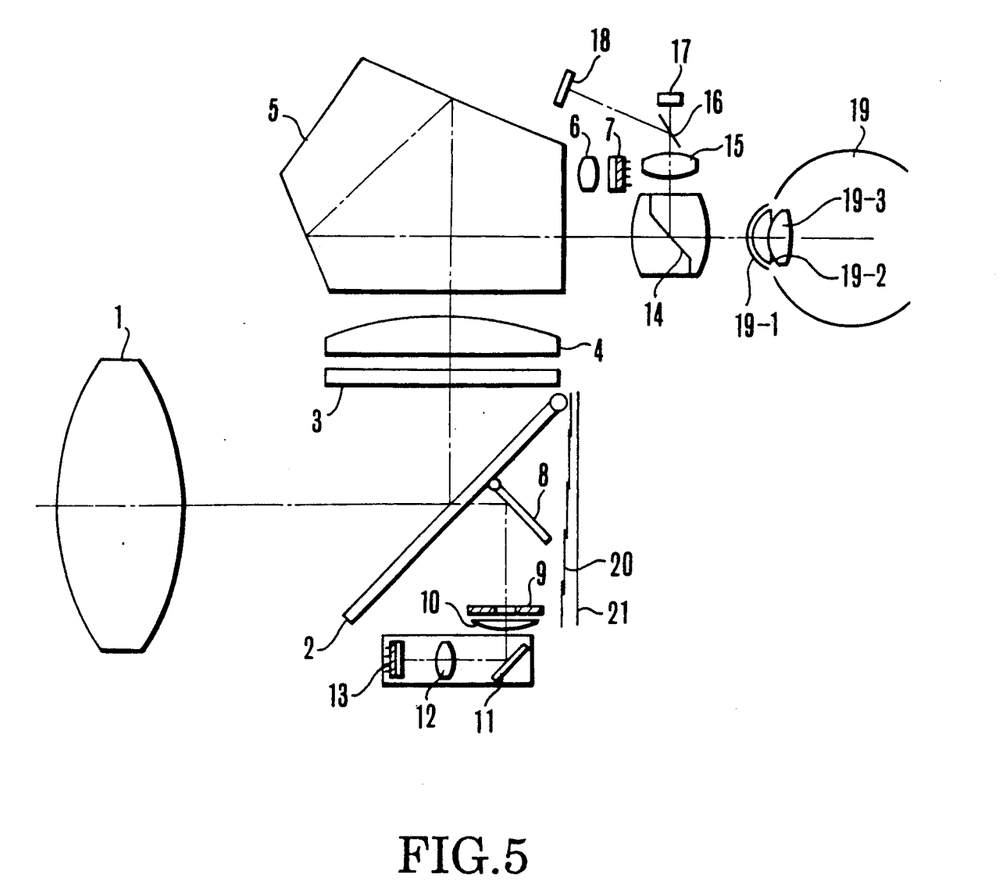
FIG. 5 is an optical block diagram showing a camera provided with a visual line detecting device arranged according to this invention as an embodiment thereof.

FIG. 5 shows by way of example the optical block of the camera having the visual line detecting device arranged according to this invention. The illustration includes a photo-taking lens 1, a quick-return mirror 2; a focusing screen 3; a condenser lens 4; a pentagonal prism 5 which forms an ordinary viewfinder optical system; a condenser lens 6 for light measurement; and a light measuring element 7 which is arranged to form a light measuring system in conjunction with the viewfinder system.

FIG. 5 further includes a sub-mirror 8; a field mask 9; a field lens 10; an AF (automatic focusing) light-flux bending mirror 11; a secondary image forming lens 12; and a photo-electric conversion element 13. These members jointly form a focus detection system.

Meanwhile, a visual line detecting device is formed jointly by an eyepiece lens 14 including a beam splitter which transmits visible rays of light and reflects infrared rays; a light-projecting and -receiving lens 15; a beam splitter 16; an infrared ray projecting LED 17; and a linear- or area-type photo-electric conversion element 18 which is a CCD or the like. A reference numeral 19 denotes an eye of the photographer including a cornea 19-1; an iris 19-2; and a crystalline lens 19-3. Further, a numeral 20 denotes a shutter and 20 a film.

The rays projected from the infrared ray LED 17 are converted into a parallel flux of rays to irradiate the eye 19 therewith. Then, the cornea 19-1 and the iris 19-2 of the eye 19 reflect the incident infrared rays. The reflected rays are arranged to be imaged on the photo-electric conversion element 18 through the lens 15.

Since the eye is almost completely insensitive to the infrared rays used for visual line detection, the infrared rays cause no change in the pupil diameter. The pupil diameter is controllable only by light coming from the viewfinder system. This enables the device to obtain information on the pupil diameter of the photographer by means of a signal output from the light measuring element 7.

In order to enhance the degree of safety of the visual line detecting system, the energy of the infrared rays to be applied to the eye 19 is preferably reduced. To meet this requirement, the beam splitter 16 is arranged to have a larger visible transmission factor and a larger infrared reflection factor in such a way as to have the reflection light from the eye almost completely imaged on the photo-electric conversion element 18. This arrangement permits reduction to a minimal degree the amount of infrared rays to be used for irradiating the eye 19, and has no adverse influence on the viewfinder system of the camera.

Figure 6A:
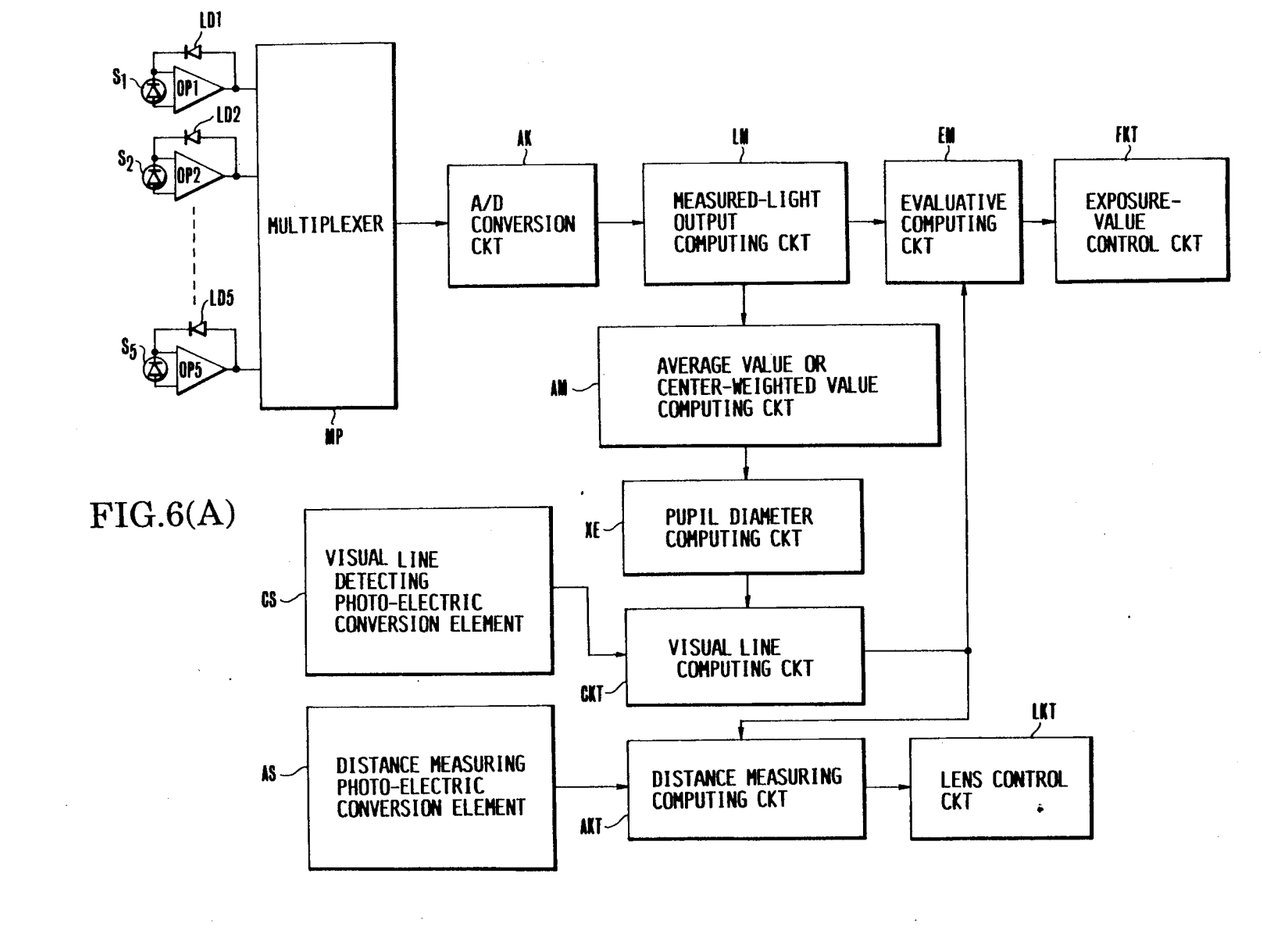
FIG. 6(A) is a block diagram showing the electrical circuit arrangement of the embodiment shown in FIG. 5.

FIG. 6(A) is a block diagram showing by way of example an electric circuit to be used in supplying information on the visual line to the camera by means of the invented visual line input device described above. In FIG. 6(A), reference symbols S1 to S5 denote photo-electric conversion elements which are arranged to measure the light of divided areas of a photo-taking image plane. Symbols LD1 to LD5 denote logarithmic conversion elements. Symbols OP1 to OP5 denote operational amplifiers. Photo-electric conversion circuits are formed respectively by these elements. The outputs of these photo-electric conversion circuits are time serially analog-to-digital (AD) converted by an AD conversion circuit AK through a multiplexer MP. As a result, measured light outputs corresponding to these photo-electric conversion elements S1 to S5 are produced by a measured-light output computing circuit LM. These outputs of the circuit LM are supplied to an average value or center-weighted value computing circuit AM. The circuit AM then produces an average value or a center-weighted value of the measured light values. A pupil diameter computing circuit XE then computes and produces the diameter of the pupil on the basis of the output of the circuit XE. A visual line computing circuit CKT performs a computing operation on information obtained from the pupil diameter computing circuit XE and information obtained from the visual line detecting photo-electric conversion element CS (the element 18 of FIG. 5). As a result, the visual line computing circuit CKT produces information on the direction of the visual line. The output of the visual line computing circuit CKT is supplied to an evaluative computing circuit EM. The circuit EM is arranged to perform computation on the basis of the output of the circuit CKT and correct the measured light value in such a way as to have it weighted in the direction of the visual line. The output of the evaluative computing circuit EM is supplied to an exposure value control circuit FKT. The control of the exposure is thus performed, on the one hand, according to the result of the computing operation of the evaluative computing circuit EM.

On the other hand, the output of a photo-electric conversion element AS (the photo-electric conversion element 13 of FIG. 5) is arranged to be supplied to a distance measuring computing circuit AKT. The circuit AKT which is arranged to compute a measured distance then performs a computing operation on a part of the output of the element AS corresponding to the direction of the visual line. The output of the distance measuring circuit AKT is supplied to a lens control circuit LKT to have the position of the lens controlled according to the result of the computing operation of the circuit AKT.

Figure 6B:
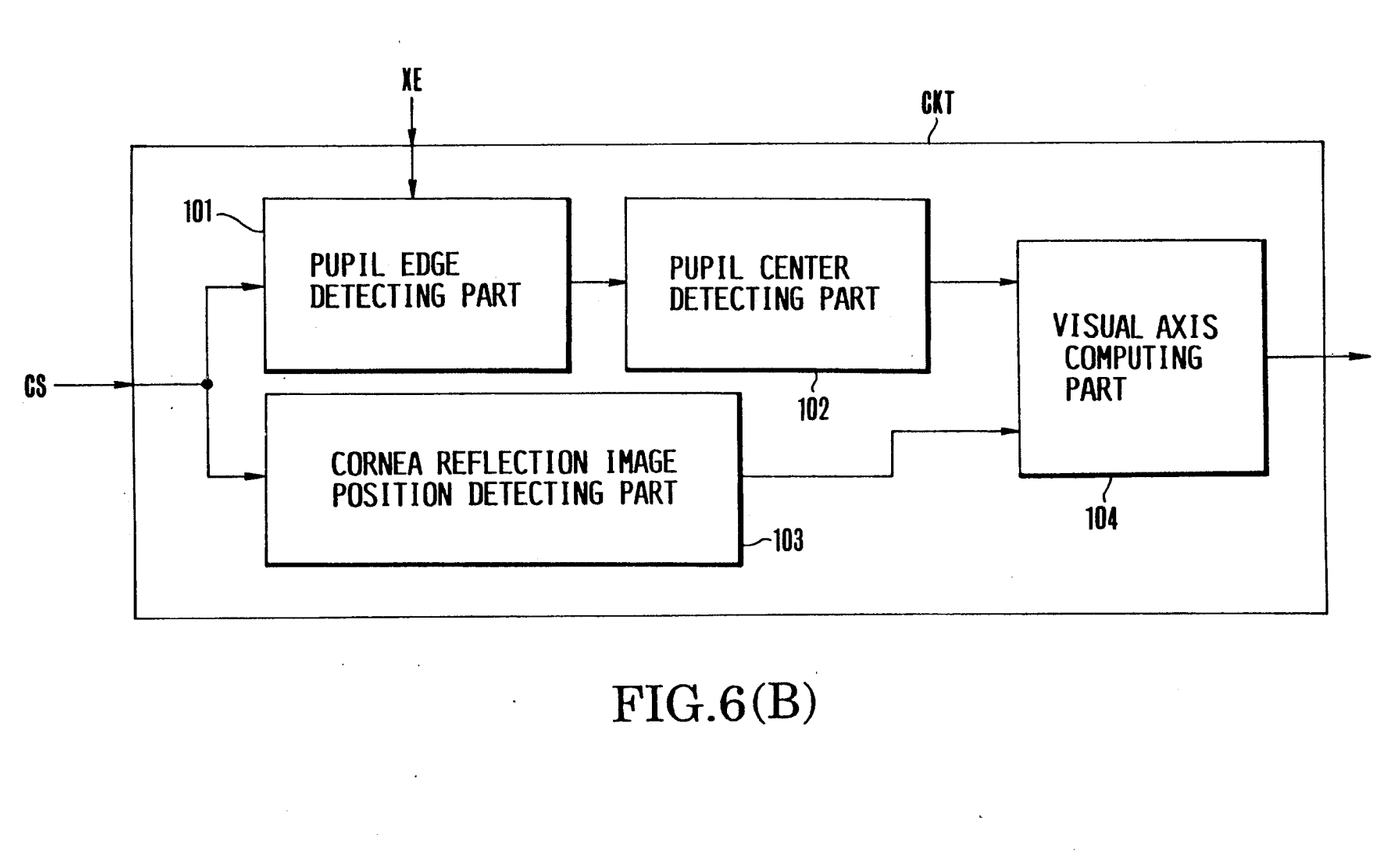
FIG. 6(B) is a block diagram showing the visual line computing circuit of the same embodiment.

FIG. 6(B) shows by way of example the details of the visual line computing circuit CKT. Referring to FIG. 6(B), a pupil edge detecting part 101 is arranged to detect the edge of the pupil by making reference to the information obtained from a visual line detecting photo-electric conversion element CS and information on the pupil diameter obtained from the pupil diameter computing circuit XE. A pupil center detecting part 102 is arranged to detect the center of the pupil on the basis of the output of the pupil edge detecting part 101. A cornea reflection image position detecting part 103 is arranged to detect the position of the reflected image of the cornea. A visual axis computing part 104 is arranged to detect the direction of the visual line on the basis of the pupil center and the cornea reflection image position (a first Purkinje image).

Figure 7A:
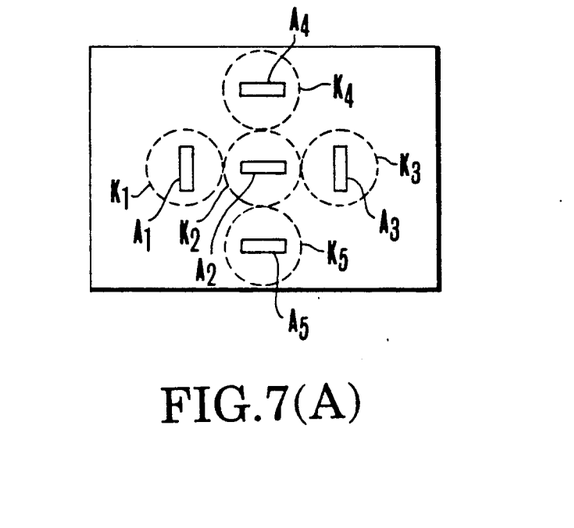
FIG. 7(A) shows a multi-point distance measuring part.
Figure 7B:
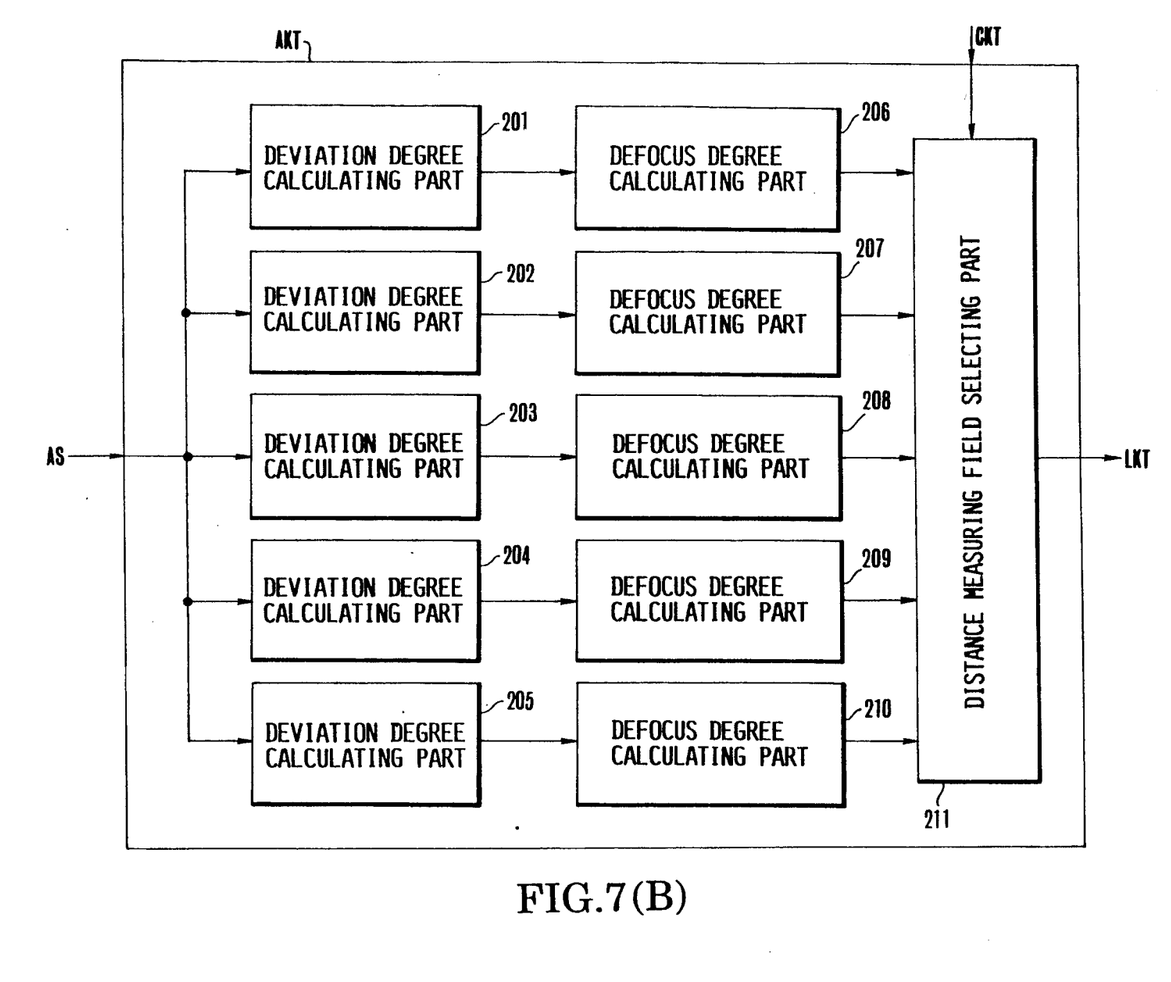
FIG. 7(B) is a block diagram showing a distance measuring computing circuit.

The distance measuring method of the embodiment is as follows: Referring to FIG. 7(A), there are five distance measuring points within the image plane. For these five distance measuring points, there are provided distance measuring parts A1 to A5. The embodiment is thus arranged to be capable of performing a focusing action for five different distance measuring points of objects to be photographed. When the visual line of the photographer is within any of visual line detecting field parts K1 to K5 surrounding these distance measuring points, the distance measuring computing circuit AKT drives the lens control circuit LKT with the object existing at this specific distance measuring point assumed to be the main object. FIG. 7(B) shows by way of example the internal arrangement of the distance measuring computing circuit AKT.

Referring to FIG. 7(B), there are provided deviation degree calculating parts 201 to 205. Each of these parts 201 to 205 is arranged to calculate a degree of discrepancy in position between two images by carrying out a correlation computing operation based on a distance measuring principle which will be described later herein. Defocus degree calculating parts 206 to 210 are arranged to calculate and obtain the defocus degree of the photo-taking lens from the deviation degree output from each of the deviation degree calculating parts 201 to 205. A distance measuring field selecting part 211 is arranged to select one of the distance measuring fields A1 to A5 on the basis of information on the direction of the visual line computed by the visual line computing circuit 211. The lens control circuit LKT is arranged to control and cause the photo-taking lens to be driven in such a way as to bring to a minimal value the defocus degree obtained from one of sensors, or photo-electric conversion elements, corresponding to the distance measuring field selected (from among the parts 206 to 210) by the distance measuring field selecting part 211.

Figure 8A:
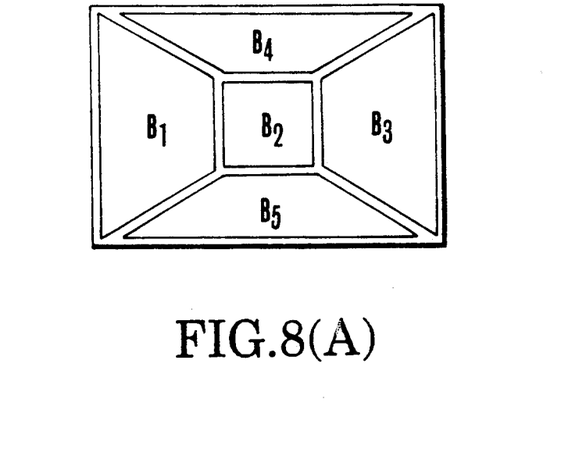
FIG. 8(A) shows a multiple light measuring part.

FIG. 8(A) shows by way of example the arrangement of a multiple light measuring part. Referring to FIG. 8(A), the multiple light measuring part consists of divided light measuring parts B1 to B5. If the visual line enters the range of a visual line detecting field K1, for example, the evaluative computing circuit EM performs an evaluative weight attaching operation in such a way as to increase the weight of the light measuring part B1.

Figure 8B:
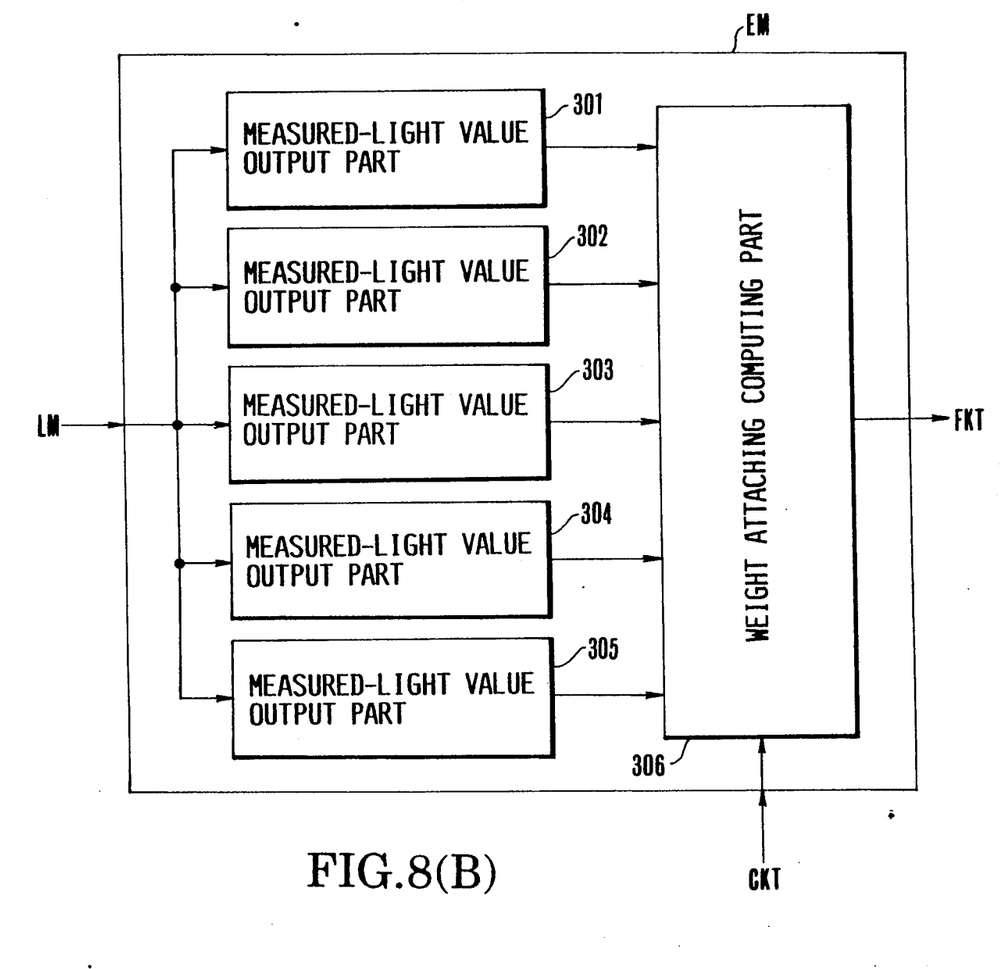
FIG. 8(B) shows in a block diagram an evaluative computing circuit.

FIG. 8(B) shows by way of example the internal arrangement of the evaluative computing circuit EM. In FIG. 8(B), reference numerals 301 to 305 denote measured-light value output parts corresponding to the photo-electric conversion elements S1 to S5. A numeral 306 denotes a weight attaching computing part. The computing part 306 is arranged to perform optimum weight attaching photometric computation according to the contrast obtained among the measured light value outputs of the parts 301 to 305. As mentioned above, the embodiment is arranged to supply the information on the direction of the visual line obtained by the visual line computing circuit CKT to the weight attaching computing part 306. Then, the part 306 performs the weight attaching computation in such a way as to attach a heavier weight to the measured light value obtained in the direction of the visual line.

Therefore, an optimum exposure can be made for a photographing object sighted by the photographer.

Figure 10A:
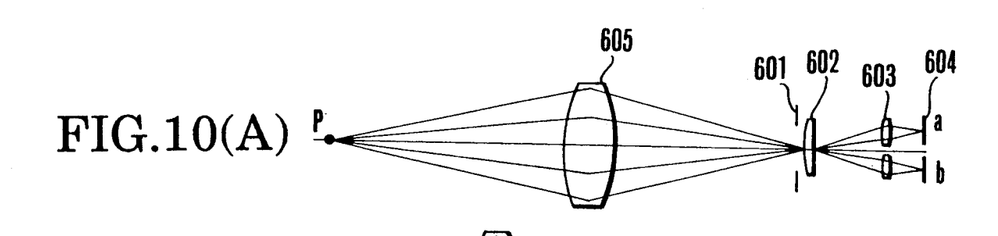
FIGS. 10(A), 10(B), 10(C), 11(A), 11(B) and 11(C) jointly show the operating principle of a focus detection system of a phase difference method.
Figure 10B:
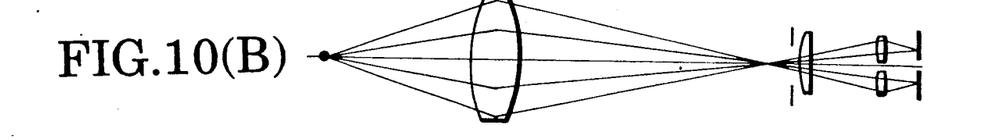
Figure 10C:
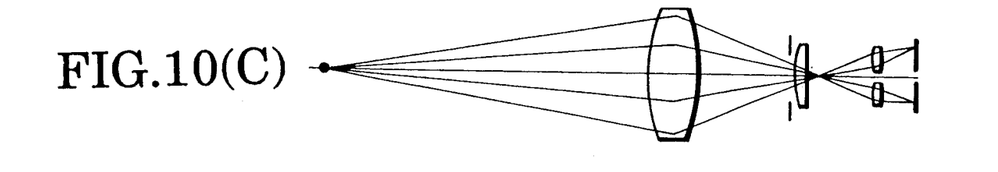
Figure 11A:
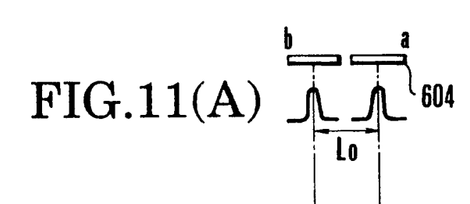
Figure 11B:
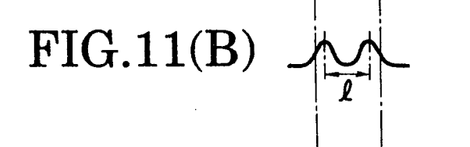
Figure 11C:
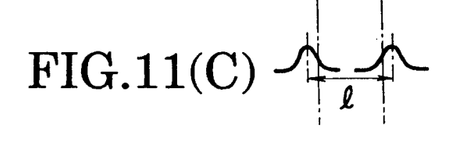

The known focus detecting methods for a single-lens reflex camera include a phase difference method. FIGS. 10(A), 10(B), 10(C), 11(A), 11(B) and 11(C) show the focus detection by the phase difference method. FIGS. 10(A), 10(B) and 10(C) show the optical path of a focus detecting optical system. FIGS. 11(A), 11(B) and 11(C) show light quantity distribution obtained on the surface of a light quantity detecting element (hereinafter referred to as a line sensor).

The illustrations include a field mask 601; a field lens 602; a secondary image forming lens 603; the line sensor 604; and a photo-taking lens 605. The field lens 602 is disposed near to the film equivalent plane of the photo-taking lens 605 (a plane equivalent to the surface of film) and is set in such a position as to satisfy a given conjugate relation between the exit pupil of the photo-taking lens 605 and the entrance pupil of the secondary image forming lens 603. A diaphragm which is not shown is disposed close to the entrance pupil face of the secondary image forming lens 603. The diaphragm is arranged to be in such a size that a light flux passing through its aperture is not eclipsed within the photo-taking lens 605.

The light of an object to be photographed which is emitted from a light source point P on the optical axis of the photo-taking lens 605 comes via the photo-taking lens 605 to be imaged around the field mask 601. The object light which passes through the aperture of the field mask 601 passes through the field lens 602 to be converged by the secondary image forming lens 603. The converged object light is then projected on the line sensor 604. In this instance, the aperture of the field mask 601 corresponds to a focus detecting area set on a photo-taking image plane. The mask 601 is thus arranged to block any light coming from the outside of the focus detecting area from being guided to the line sensor 604. The focal length and the position of the secondary image forming lens 603 are set in such a manner that an object's image which is formed on the film equivalent plane of the photo-taking lens 605 is imaged again on the line sensor 604 at a given rate of magnification. Further, the secondary image forming lens 603 has its component parts arranged in parallel in symmetrically decentered positions relative to the optical axis of the photo-taking lens 605. These parts of the secondary image forming lens 603 are arranged to receive light fluxes from different areas within the exit pupil of the photo-taking lens 605 and to form images on the parts "a" and "b" of the line sensor, each of which consists of a pair of parts.

FIG. 10(A) shows the position of the photo taking lens 605 and the film equivalent plane relative to the object P, i.e., the light source point, as in a state of satisfying an in-focus condition. In this instance, the light quantity distribution on the line sensor 604 is as shown in FIG. 11(A). As shown, a sharp peak appears approximately in the middle part of each of the line sensor parts "a" or "b". A reference symbol Lo denotes a distance between the two peak positions. The distance value Lo is an independent value which is determined by the arrangement of the focus detecting optical system.

FIG. 10(B) shows the optical path as in a near-focus state in which the photo-taking lens 605 is drawn out forward. In this case, the light quantity distribution on the line sensor 604 has a less degree of sharpness as shown in FIG. 11(B). A distance l obtained between the peaks of light quantity distribution on the line sensor parts "a" and "b" is shorter than the distance Lo. A difference $\Delta l$ ($=l-Lo$) in the distance between peak positions correlates with the defocus degree of the photo-taking lens 605. Therefore, the focus detecting action can be accomplished on the basis of this difference $\Delta l$.

FIG. 10(C) shows the optical path as in a rear-focus state in which the photo-taking lens 605 is drawn in toward the film equivalent plane. In that case, the light quantity distribution on the line sensor 604 has a less degree of sharpness and the distance l between peaks of light quantity distribution on the line sensor parts "a" and "b" is wider than the distance Lo as shown in FIG. 11(C). The difference $\Delta l$ ($=l-Lo$) in the distance between peak positions also correlates with the defocus degree of the photo-taking lens 605. Therefore, the focus detecting action can be accomplished on the basis of the difference $\Delta l$. The arrangement described thus enables the embodiment to adequately perform a focus detecting action on an ordinary object image having luminance distribution detected through the degree of difference or discrepancy ($\Delta l$) between the two images formed on the line sensor parts "a" and "b" by detecting their correlation.

Figure 12:
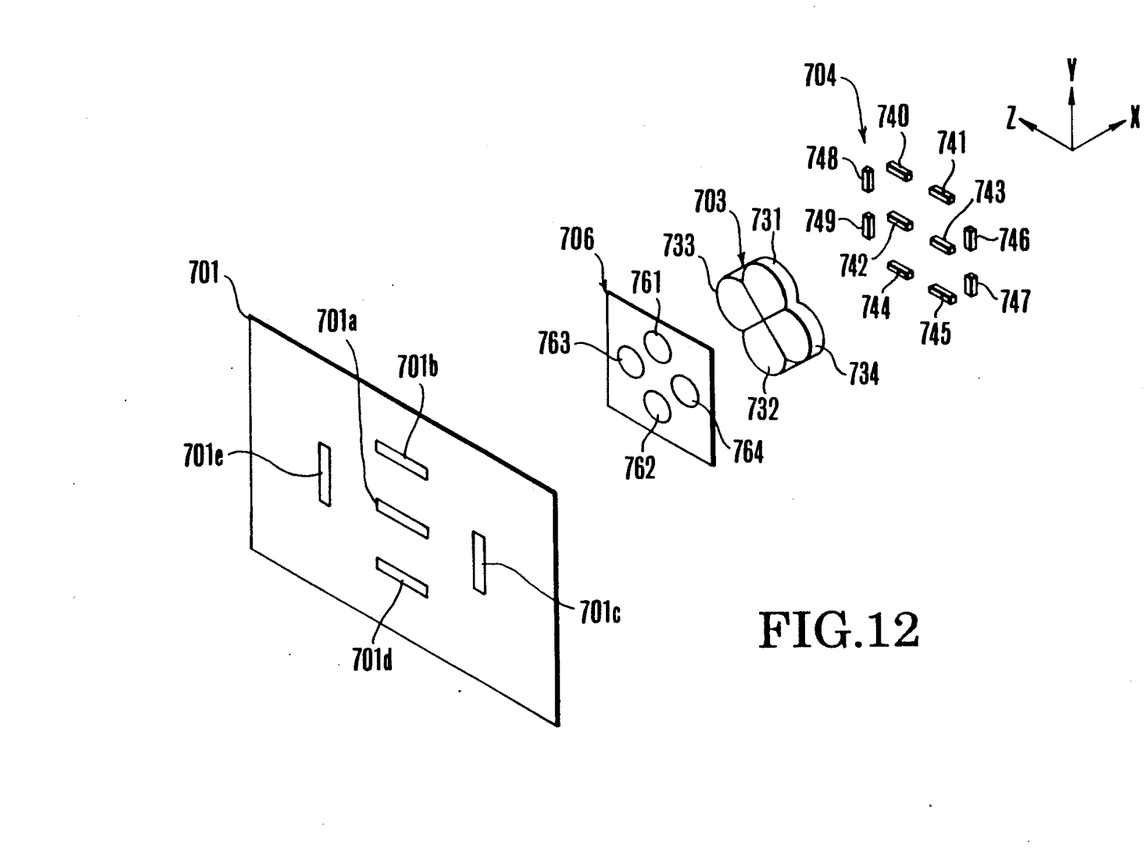
FIG. 12 is an oblique view showing light and distance measuring systems.

FIG. 12 is an oblique view showing another focus detecting optical system which is arranged to detect the focused states of a plurality of areas within an image plane. FIG. 12 includes a field mask 701; aperture parts 701a, 701b, 701c, 701d and 701e of the field mask 701; secondary image forming lenses 731, 732, 733 and 734; line sensors 740, 741, 742, 743, 744, 745, 746, 747, 748 and 749; a diaphragm 706; and the apertures 761, 762, 763 and 764 of the diaphragm. A field lens which is included in the optical system is omitted from the illustration.

The field mask 701 is disposed close to the focal plane of the photo-taking lens. Therefore, the aperture parts of the field mask 701 coincide with the focus detecting areas. The line sensor group 704 is arranged in the positions of conjugate images to be formed jointly through the secondary image forming lens group 703 and the aperture parts of the field mask.

The correlation of the aperture parts of the field mask 701 with the secondary image forming lens group 703 and the line sensor group 704 is as shown in Table 1 below:

TABLE 1

| Apertures of field mask 701 | Apertures of diaphragm 706 | Secondary image forming lens group 703 | Line sensor group 704 |
| --- | --- | --- | --- |
| 701a | 763 | 733 | 742 |
|  | 764 | 734 | 743 |
| 701b | 763 | 733 | 744 |
|  | 764 | 734 | 745 |
| 701c | 761 | 731 | 748 |
|  | 762 | 732 | 749 |
| 701d | 763 | 733 | 740 |
|  | 764 | 734 | 741 |
| 701e | 761 | 731 | 746 |
|  | 762 | 732 | 747 |

The focus detection optical system arranged in this manner is capable of detecting, in the same manner as in the case of the preceding example of the optical system described in the foregoing, the focus position of each of the different distance measuring field parts by obtaining the correlation between the output signals of paired line sensors 742 and 743; 744 and 745; 748 and 749; 740 and 741; and 746 and 747.

As described in the foregoing, the visual line detecting device according to this invention is capable of detecting, with a high degree of accuracy, the deteriorated resolution of the position of the boundary between the pupil and the iris from the image information obtained through image sensing means by virtue of the arrangement to take into consideration the information on an estimated pupil diameter. Therefore, the center position of the pupil can be accurately detected and thus the direction of the visual line also can be accurately detected.

Further, a camera having the visual line detecting device of this embodiment uses the light measuring circuit of the camera in estimating the pupil diameter. Therefore, the pupil diameter can be estimated under the same condition as when the photographer looks into the viewfinder. This ensures that the direction of the visual line can be accurately detected even in the event of inadequate contact of the eye of the photographer with the viewfinder.

What is claimed is:

1. A visual line detecting device arranged to detect a Purkinje image position of an illuminated eye through light reflected by the eye and to detect the direction of a visual line on the basis of the Purkinje image position and a position of the center of a pupil, comprising:
   a) means for estimating a diameter of the pupil of the eye from the luminance of external light; and
   b) means for determining said position of the center of the pupil by determining a position of a boundary between the pupil and an iris of the eye on the basis of the estimated diameter of the pupil.

2. A device according to claim 1, wherein the diameter of the pupil is estimated through a computing operation performed by a pupil diameter computing circuit on the basis of an output of light measuring means.

3. A device according to claim 2, wherein said light measuring means is arranged to detect a part of said external light obtained from an area approximately coinciding with the direction of the line of sight.

4. A visual line detecting device for detecting the direction of a visual line, by detecting an image position of a tissue of an illuminated eye on the basis of light reflected by the eye, on the basis of said image position and a position of the center of a pupil of the eye, comprising:
   a) means for estimating a diameter of the pupil of the eye from the luminance of external light; and
   b) means for determining said position of the center of the pupil by determining a position of a boundary between the pupil and an iris of the eye on the basis of estimated diameter of the pupil.

5. A device according to claim 4, wherein the diameter of the pupil is estimated through a computing operation performed by a pupil diameter computing circuit on the basis of an output of light measuring means.

6. A device according to claim 5, wherein, to detect the direction of the visual line, information is obtained about the position of said boundary between said pupil and said iris obtained from said estimated diameter of the pupil, the center of said pupil is obtained on the basis of said boundary position information, and said direction of the visual line is detected from a Purkinje image (a position of a reflection light image of a cornea of the eye) and information on said center of the pupil.

7. A camera having a visual line detecting device, comprising:
   a) illuminating means for illuminating an eye;
   b) image detecting means for detecting an image position of a tissue of the eye from light reflected by the eye illuminated by said illuminating means;
   c) light measuring means for detecting the luminance of external light;
   d) pupil diameter estimating means for estimating a diameter of a pupil of the eye on an basis of an output of said light measuring means; and
   e) computing means for determining a position of a boundary between the pupil and an iris of the eye on the basis of information on the diameter of the pupil estimated by said pupil diameter estimating means to estimate a position of the center of the pupil, and for detecting the direction of the visual line on the basis of said image position detected by said image detecting means and said position of the center of the pupil.

8. A camera according to claim 7, wherein said illumination means includes a light emitting element disposed close to a viewfinder of said camera and a reflection member arranged to reflect light emitted by said light emitting element toward the eye.

9. A camera according to claim 7, wherein said image detecting means is arranged to detect at least a position of a Purkinje image and a position of an image of another tissue of the eye.

10. A camera according to claim 9, wherein said image detecting means is arranged to detect at least a position of a Purkinje image from a light quantity distribution of said reflection light.

11. A camera according to claim 7, wherein said light measuring means is arranged to detect, with a light measuring element, external light obtained in an area of a viewfinder of the camera.

12. A camera according to claim 7, wherein said light measuring means is arranged to detect, with a light measuring element, light of a photographing object coming through a photo-taking lens.

13. A camera according to claim 11, wherein said light measuring means includes a plurality of light measuring elements and is arranged to perform a computing operation on an output of each of said plurality of light measuring elements to obtain an output which is supplied to said pupil diameter estimating means.

14. A camera according to claim 12, wherein said light measuring means includes a plurality of light measuring elements and is arranged to perform a computing operation on an output of each of said plurality of light measuring elements to obtain an output which is supplied to said pupil diameter estimating means.

15. A camera according to claim 9, wherein said computing means is arranged to detect the direction of the visual line from the position of said Purkinje image and that of said center of the pupil.

16. A camera according to claim 7, further comprising distance measuring means for measuring distances by dividing a photographing field into a plurality of areas, said distance measuring means being arranged to determine, on the basis of the direction of the sight of line detected by said computing means, which of the measured distances of said areas is to be used as a measured distance information output for shifting the position of a photo-taking lens.

17. A camera according to claim 7, further comprising light measuring means for measuring light by dividing a photographing field into a plurality of areas, said light measuring means being arranged to vary the degree of weight to be attached to a measured light output for each of said divided areas on the basis of the direction of the sight of line detected by said computing means.

18. A camera according to claim 16, wherein said image detecting means is arranged to detect at least a position of a Purkinje image and a position of an image of another tissue of the eye.

19. A camera according to claim 17, wherein said image detecting means is arranged to detect at least a position of a Purkinje image and a position of an image of another tissue of the eye.

20. A camera according to claim 18, wherein said computing means is arranged to detect the direction of the visual line from the position of said Purkinje image and that of said center of the pupil.

21. A camera according to claim 19, wherein said computing means is arranged to detect the direction of the visual line from the position of said Purkinje image and that of said center of the pupil.

22. A camera according to claim 8, further comprising distance measuring means for measuring distances by dividing a photographing field into a plurality of areas, said distance measuring means being arranged to determine, on the basis of the direction of the sight of line detected by said computing means, which of the measured distances of said areas is to be used as a measured distance information output for shifting the position of a photo-taking lens.

23. A camera according to claim 8, further comprising distance measuring means for measuring distances by dividing a photographing field into a plurality of areas, said distance measuring means being arranged to determine, on the basis of the direction of the sight of line detected by said computing means, which of the measured distances of said areas is to be used as a measured distance information output for shifting the position of a photo-taking lens.

24. A camera according to claim 11, further comprising second light measuring means for measuring the luminance of a photographing object for exposure control, said second light measuring means including a light measuring element which serves also as said light measuring element of said light measuring means.

25. A camera according to claim 13, further comprising second light measuring means for measuring the luminance of a photographing object for exposure control, said second light measuring means having a plurality of light measuring elements which serve also as said plurality of light measuring elements of said light measuring means.

* * * * *